United States Patent [19]

Lehmbeck

[11] 4,253,468

[45] Mar. 3, 1981

[54] NEBULIZER ATTACHMENT

[76] Inventor: Steven Lehmbeck, 48 Prospect St., Hawthorne, N.J. 07506

[21] Appl. No.: 933,202

[22] Filed: Aug. 14, 1978

[51] Int. Cl.³ ............................................ A61M 16/00
[52] U.S. Cl. ............................. 128/726; 128/200.18; 128/200.21
[58] Field of Search ............... 128/194, 201, 208, 188, 128/145.6, 145.8, 185, 173 R, 193, 195, 196, 197, 202, 205, 206, 207, 209, 210, 727, 726, 725, 716, 187, 200.21, 200.22, 200.14, 203.28

[56] References Cited

U.S. PATENT DOCUMENTS

| 864,908 | 9/1907 | Nebelthau | 128/726 |
| 895,606 | 8/1908 | Wande | 128/726 |
| 3,172,406 | 3/1965 | Bird et al. | 128/173 R |
| 3,826,255 | 7/1974 | Havstad et al. | 128/194 |

FOREIGN PATENT DOCUMENTS

| 181355 | 3/1955 | Austria | 128/188 |
| 845836 | 7/1949 | Fed. Rep. of Germany | 128/200.21 |
| 367491 | 3/1908 | France | 128/188 |

*Primary Examiner*—Henry J. Recla

*Attorney, Agent, or Firm*—Jordan and Hamburg

[57] ABSTRACT

Two attachments are provided for a nebulizer which is used to administer a liquid medication in aerosol form to the respiratory tract of a patient by inhalation. One attachment is a reservoir which is interposed between the nebulizer and the patient's mouth for trapping and returning to the nebulizer liquid medication which separates from the aerosol. The other attachment is for use when the nebulizer is used in combination with a spirometer. The spirometer comprises a conduit containing a rotor. The inhaled air causes the rotor to spin, the air then mixes with the aerosol produced by the nebulizer and the mixture of air and aerosol is inhaled by the patient. The second attachment is a one-way valve interposed between the spirometer rotor and the point at which the aerosol is introduced into the air stream and is arranged to permit the passage of air only in the direction of inhalation whereby contamination of the spirometer rotor by the medication is prevented. An especially desirable apparatus is attained when the nebulizer is used in conjunction with both of the aforementioned attachments.

3 Claims, 3 Drawing Figures

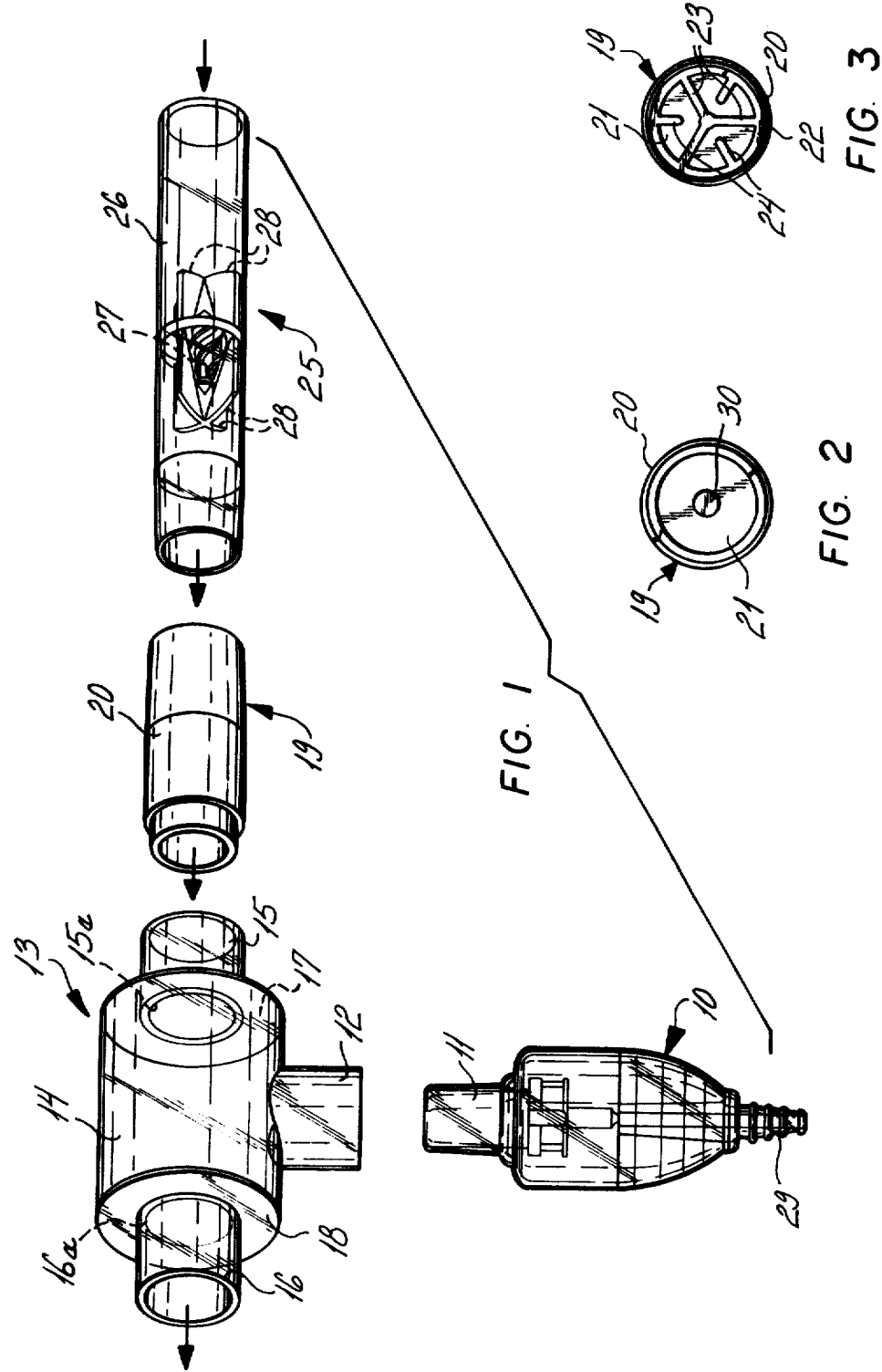

NEBULIZER ATTACHMENT

BACKGROUND OF THE INVENTION

This invention relates to attachments for nebulizers for the administration to patients of liquid medication in aerosol form by inhalation.

Certain problems exist in the administration of liquid medications to the respiratory tracts of patients by the use of nebulizers to place the liquid medication in aerosol form in which the liquid medication can readily be inhaled. One problem relates to the fact that between the nebulizer and the patient's mouth, some of the liquid medication separates from the aerosol. The liquid medication may escape from the system whereby the patient receives less, by some indeterminate amount, than the prescribed dosage. On the other hand, the patient may swallow the liquid medication which has separated from the aerosol. This subjects the patient to a sudden, relatively massive dosage of the medication, which can have undesirable side effects, and, moreover, a portion of the medication which was intended for inhalation into the respiratory tract has now been diverted to the alimentary tract, which is a major departure from the prescribed treatment.

Another problem concerning nebulizers relates to their use in conjunction with spirometers. A spirometer is a device for measuring air flow. The patient breathes in the aerosol along with ambient air. In certain treatments, it is desired to measure the rate at which the patient is inhaling ambient air. The spirometer typically comprises a conduit in which is mounted a rotor which is rotated by the inhaled air. This is used in conjunction with a source of light and a photoelectric cell between which the conduit, which is transparent, is interposed to determine the rate of rotation of the rotor and, thereby, the rate of air flow through the conduit containing the rotor. The spirometer rotor is located upstream from the point at which the aerosol is introduced into the air stream being inhaled, since the medication would follow the rotor, impairing its accuracy and perhaps even eventually preventing its rotation at all. As noted above, some of the liquid medication tends to separate from the aerosol. Apart from escaping the system or being swallowed by the patient, this liquid medication can find its way to the rotor despite the fact that it initially is downstream from the rotor.

It is an object of the invention to provide attachments for use with nebulizers for the purpose of overcoming the aforementioned problems.

Other objects and advantages of the invention will be apparent from the following description thereof.

SUMMARY OF THE INVENTION

According to the invention, there is provided for use with a nebulizer an attachment serving as a reservoir for trapping liquid medication which separates from the aerosol, thereby permitting the liquid medication to return to the nebulizer for reconversion into aerosol form. A conventional nebulizer has an outlet for aerosol, the nebulizer when used by a patient being adapted to be oriented substantially vertically with the outlet at the top. In some conventional arrangements, the nebulizer is used in conjunction with a T-connector conduit. The vertical leg of the T constitutes an inlet for aerosol from the nebulizer, which is mated with the nebulizer outlet. The two ends of the horizontal part of the T constitute, respectively, an inlet for communication with the ambient for supplying air for inhalation by the patient together with the aerosol and an outlet in substantial axial alignment with the inlet for communication with the patient's mouth. In many cases, the inlet for communication with the ambient is mated with a conduit containing a spirometer rotor, the aforementioned inlet communicating with the ambient through that conduit.

In a preferred embodiment of the present invention, the aforementioned reservoir is provided essentially in the form of a modification of the aforementioned T-connector conduit. The modification comprises end walls through which the inhalation inlet and outlet are formed. Typically the end walls are annular. Thus a reservoir is formed by the horizontal portion of the T between the annular walls. The annular walls, in particular the bottom portion thereof, prevent liquid medication from flowing into the inhalation inlet and outlet, trapping the liquid medication which separates from the aerosol. The trapped liquid medication will simply flow into the vertical arm of the T, back down into the nebulizer for reconversion into aerosol form.

According to another aspect of the invention, an attachment is provided to prevent fouling by liquid medication of the aforementioned spirometer rotor. This attachment is in the form of a conduit in which is mounted a one-way valve. This conduit is mated at one end with the inhalation inlet of a T-connector, whether it be the conventional T-connector or a T-connector in which is formed a reservoir according to the first mentioned aspect of the present invention, and at the other end with the conduit in which is mounted a spirometer rotor. The one-way valve is arranged to permit the passage of air only in the direction from the ambient toward the inhalation inlet whereby contamination of the spirometer rotor by the liquid medication is prevented. It is noteworthy that even the presence of the reservoir attachment does not completely eliminate the possibility of contamination of the spirometer rotor. For example, the patient may accidentally propel the aerosol toward the spirometer rotor by exhaling while the inhalation inlet is still in his mouth. Thus, the use of both attachments with a conventional nebulizer results in the optimum device.

BRIEF DESCRIPTION OF THE DRAWINGS

FIG. 1 is an exploded isometric view of an assembly constituted of a conventional nebulizer, a reservoir attachment according to the invention, a one-way valve attachment according to the invention, and a conventional spirometer;

FIG. 2 is an end view of the one-way valve attachment viewed in the direction in which the valve does not open; and FIG. 3 is the other end view of the one-way valve attachment, this view being in the direction in which the valve opens.

DETAILED DESCRIPTION OF THE PREFERRED EMBODIMENTS

All of the parts which shall now be described, are, in the particular embodiment here illustrated, transparent except for the one-way valve attachment and the spirometer rotor. Whether or not the one-way valve attachment is transparent is immaterial. The spirometers are generally made transparent so that the level of medication therein can be observed. It is not critical that the reservoir attachment be made transparent but this can be useful for the purposes of monitoring the operation of the device. In the conventional spirometer, at least the portion of the conduit surrounding the spirometer housing must be transparent in order to implement the principle of the spirometer. More particularly, the conventional spirometer rotor is provided with an orifice. Light from a conventional source of illumination is beamed perpendicularly through the transparent housing across the path of the rotor to a photoelectric cell located at the other side of the housing. The rotor is fabricated of a non-transparent material. Consequently, the light which is beamed at the rotor can pass through the rotor only twice each revolution of the rotor, i.e. each time the aforementioned orifice comes into alignment with the light path. These occurrences are sensed by the photoelectric cell, whereby the rate of rotation of the rotor is sensed. This, in turn, is related directly to the rate of the air flow through the conduit containing the spirometer rotor. Plastics are commonly used for conventional nebulizers and spirometers and are also the preferred materials of construction for the attachments according to the present invention.

With reference to FIG. 1, the nebulizer 10 is of conventional construction and, accordingly, will not be described herein in detail. A complete, detailed description of the nebulizer 10 can be found in U.S. Pat. No. 3,762,409. The nebulizer 10 includes an aerosol outlet 11. In actual use, the nebulizer 10 is oriented with its axis of symmetry essentially vertical, or at least upright, as illustrated in FIG. 1, so that the liquid medication is retained in the nebulizer until it is converted into aerosol form.

The aerosol outlet 11 of the nebulizer 10 is mated with an inlet 12 of a reservoir attachment 13 according to the present invention. The reservoir attachment 13 is in the general configuration of a T-connector. The aforementioned inlet 12 constitutes the intermediate, vertical leg of the T. The horizontal portion of the T is constituted of the cylindrical reservoir 14 and respective axially aligned inlet 15 and outlet 16 communicating therewith. The reservoir 14 has respective end walls 17 and 18 in which are formed respective inlet opening 15a and outlet opening 16a, with which respective inlet 15 and outlet 16 communicate.

Mating with the inlet 15 is a one-way valve attachment according to the invention. The one-way valve itself is contained in a conduit 20. The construction of the one-way valve itself is shown in FIGS. 2 and 3. The arrows in FIG. 1 show the direction of inhalation by the patient. FIG. 2 is an end view of the attachment 19 taken from the downstream end, i.e. the end which is at the left in FIG. 1. FIG. 3 is an end view taken from the opposite end. About midway between the ends of the conduit 20 is located a thin, light, flexible membrane 21 of elastomeric material, such as rubber or an elastomeric plastic, such materials being very well known and commonly available. An annular lip 22 is formed on the inside wall of the confuit 20 and a perimeter annular area of the membrane 21 rests on the annular lip 22, the annular lip 22 constituting the valve seat, whereby the valve is closed. On the upstream side of the membrane 21, radiating from and integral with the lip 22 is a three-leged web 23 and three arms 24, the legs of the web 23 being spaced from each other by 120° and the arms 24 being located midway between the legs. The membrane 21 rests on the web 23 and the arms 24, as well as the lip 22, and is thereby prevented from sagging in the middle.

An axial pin (not illustrated) is integrally formed at the center of the web 23 and is received in an orifice of substantially the same diameter (not illustrated) through the center of the membrane 21. A cap 30 is press-fit on the pin at the downstream side of the membrane 21 to hold the membrane 21 fixed at its center under all conditions.

Mated with the upstream end of the valve 20 is a conventional spirometer 25. The spirometer 25 is constituted of a conduit 26 in which is axially rotatably supported a rotor 27 by webs 28. The spirometer operates by the principle described hereinabove.

The patient to be treated receives the outlet 16 in his mouth. Compressed air or other inhalable compressed gas is introduced into the nebulizer 10, which has been charged with liquid medication, through a line (not illustrated) leading to the source of compressed gas (not illustrated). The aerosol generated by the nebulizer 10 feeds through the inlet 12 into the reservoir 14 from which it is inhaled by the patient. Any liquid medication which separates from the aerosol falls to the bottom of the reservoir, in which it is trapped by the end walls 17 and 18, and flows back through the reservoir inlet 12 and nebulizer outlet 11 into the nebulizer 10, where it is again transformed into aerosol form. With reference to the one-way valve attachment 19, the periphery of the membrane 21 lifts from the valve seat 22 in response to the negative pressure created by the inhalation by the patient, thereby permitting the flow of ambient air through the one-way valve. In the reservoir 14, the stream of ambient air being inhaled mixes with the aerosol and carries the aerosol into the patient's mouth and respiratory system. While this is occurring, the spirometer rotor 27 is being rotated by the stream of ambient air being inhaled through the spirometer conduit 26, the rotation of the rotor being used to measure the rate at which the air is being inhaled, according to the principle generally described hereinabove. The one-way valve prevents fouling of the rotor 27 by liquid medication according to the principle hereinabove described.

If desired, the reservoir 14 may be of slightly greater diameter at the mid-portion thereof through which the inlet 12 passes in order to create a slope toward the inlet 12 which will aid the draining back into the nebulizer of liquid medication which has separated from the aerosol. As generally noted hereinabove, the one-way valve attachment 19 would also be useful with a conventional T-connector used instead of the reservoir attachment according to the invention. Also, the one-way valve could be fabricated as part of the inlet 15, thus dispensing with a separate one-way valve attachment. In another alternative, the inlet opening 15a is provided with an annular flange or nipple extending slightly inwardly from the inside of the end wall 17, i.e., as if the inlet 15 were formed on the inside of the end wall 17 instead of the outside thereof but of shorter length, and the one-way valve is formed at the downstream end of the flange, the upstream end of the flange being mutable for receiving another conduit, if desired, such as spirometer conduit 26. Other modifications and variations within the spirit of the present invention are intended to be included within the scope of the hereto appended claims.

What I claim is:

1. In combination with a nebulizer for converting liquid medication into aerosol, the nebulizer having an outlet for the aerosol, the nebulizer when used by a patient being adapted to be oriented substantially vertically with the outlet at the top, the improvement comprising a reservoir, the reservoir including a chamber having an inlet for communication with the ambient for supplying air for inhalation by the patient together with the aerosol, an outlet in substantial axial alignment with the inlet for communication with the patient's mouth, an inlet formed in the chamber floor intermediate the inhalation inlet and outlet and substantially perpendicular thereto, the intermediate inlet being connected to the nebulizer outlet and thereby being in communication with the nebulizer, end walls through which said inhalation inlet and outlet are formed, the intermediate inlet being above the nebulizer outlet when the nebulizer is being used by a patient and the end walls extending upwardly from the entire chamber floor to heights substantially above the chamber floor, the chamber floor between the end walls defining an unobstructed path for draining of liquid medication from said chamber floor into said intermediate inlet, whereby the reservoir is adapted for trapping liquid medication which separates from the aerosol, preventing the liquid medication from entering said inhalation inlet and outlet and permitting the liquid medication to drain back into the nebulizer through said intermediate inlet, a first conduit communicating with the inhalation inlet and a spirometer rotor mounted in the conduit for rotation by air drawn through the conduit by inhalation by the patient, a second conduit communicating at one end with the first conduit and communicating at the other end with the inhalation inlet, whereby the first conduit communicates with the inhalation inlet through the second conduit, and a one-way valve mounted in the second conduit, the one-way valve being arranged to permit the passage of air only in the direction from the ambient toward the inhalation inlet, whereby contamination of the spirometer rotor by the medication is prevented.

2. In combination with a nebulizer for converting liquid medication into aerosol, the nebulizer having an outlet for the aerosol, the nebulizer when used by a patient being adapted to be oriented substantially vertically with the outlet at the top, the improvement comprising a reservoir, the reservoir including a chamber having an inlet opening for communication with the ambient for supplying air for inhalation by the patient together with the aerosol, an outlet opening in substantial axial alignment with the inlet opening, an outlet conduit in axial alignment with the outlet opening, the outlet conduit having one end connected to the outlet opening and another end remote from the chamber, the outlet conduit being of smaller cross sectional area than the chamber and being adapted to be received in a patient's mouth, a chamber floor, a permanently open inlet formed in the chamber floor intermediate the inhalation inlet opening and outlet opening and substantially perpendicular thereto, the intermediate inlet being connected to the nebulizer outlet and thereby being in communication with the nebulizer, end walls through which said inhalation inlet and outlet openings are formed, the intermediate inlet being above the nebulizer outlet when the nebulizer is being used by a patient and the end walls extending upwardly from the entire chamber floor to heights substantially above the chamber floor, the chamber floor between the end walls defining an unobstructed path for draining of liquid medication from said chamber floor into said intermediate inlet, whereby the reservoir is adapted for trapping liquid medication which separates from the aerosol, preventing the liquid medication from entering said inhalation inlet and outlet and at all times permitting the liquid medication to drain back into the nebulizer through said intermediate inlet.

3. In combination with a nebulizer for converting liquid medication into aerosol, the nebulizer having an outlet for the aerosol, the nebulizer when used by a patient being adapted to be oriented substantially vertically with the outlet at the top, a T-connector conduit having an inlet for communication with the ambient for supplying air for inhalation by the patient together with the aerosol, an outlet in substantial axial alignment with the inlet for communication with the patient's mouth and an inlet intermediate the inhalation inlet and outlet and substantially perpendicular thereto for communication with the nebulizer, and a first conduit communicating with the inhalation inlet and a spirometer rotor mounted in the conduit for rotation by air drawn through the conduit by inhalation by the patient, the improvement comprising a second conduit communicating at one end with the first conduit and communicating at the other end with the inhalation inlet, whereby the first conduit communicates with the inhalation inlet through the second conduit, and a one-way valve, mounted in the second conduit, the one-way valve being arranged to permit the passage of air only in the direction from the ambient toward the inhalation inlet, whereby contamination of the spirometer rotor by the medication is prevented.

* * * * *